United States Patent [19]

Collier et al.

[11] B 4,093,945
[45] June 6, 1978

[54] BREATH TESTING SYSTEM

[75] Inventors: Donald W. Collier, Chicago; Joseph P. Hoppesch, Streamwood; Anthony C. Mamo, Arlington Heights, all of Ill.

[73] Assignee: Alcohol Countermeasure Systems, Inc., Sarnia, Canada

[21] Appl. No.: 136,921

[22] Filed: Apr. 23, 1971

[44] Published under the second Trial Voluntary Protest Program on May 29, 1976 as document No. B 136,921.

[51] Int. Cl. .......................... B60k 27/08; G08b 21/00
[52] U.S. Cl. ....................................... 340/279; 180/99; 340/52 R
[58] Field of Search ............... 340/279, 52 R; 180/99, 180/82, 82 R; 307/10 R; 73/421.5 R; 128/26

[56] References Cited

U.S. PATENT DOCUMENTS

| 3,186,508 | 6/1965 | Lamont | 340/279 |
| 3,238,783 | 3/1966 | Wright | 73/421.5 R |

Primary Examiner—John W. Caldwell
Assistant Examiner—Glen R. Swann, III
Attorney, Agent, or Firm—Richard G. Kinney

[57] ABSTRACT

A breath testing system for under-supervised or unsupervised alcohol intoxication breath testing. The system includes a breath input unit, a controller which delivers a sample of deep lung breath to an evaluator including an alcohol detector and an output apparatus. The controller includes a breath flow sensing means, e.g., a pressure sensitive switch and timer, to require a predetermined and essentially continuous and uninterrupted breath flow prior to testing to thereby insure that a lung breath sample is tested. Means for signaling failing or passing of the test are provided. A passing signal cannot be obtained unless the predetermined continuous and uninterrupted flow has occurred and the resulting sample tests below a predetermined alcohol concentration. The system is disclosed in one environment of use: in a motor vehicle, wherein failure to take or pass the test modifies the operation of the vehicle (e.g., prevents it from being driven or governs its maximum speed).

34 Claims, 14 Drawing Figures

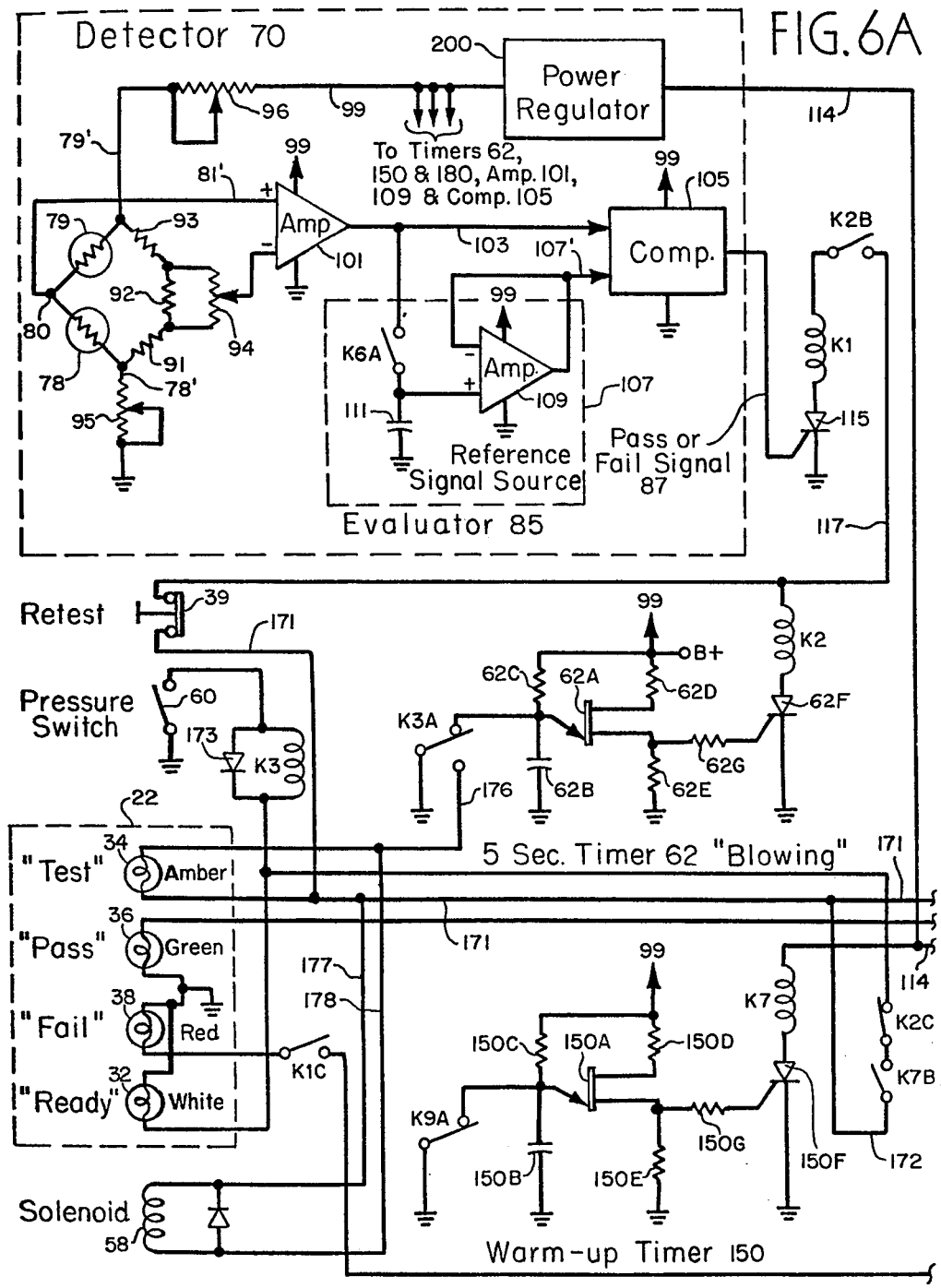

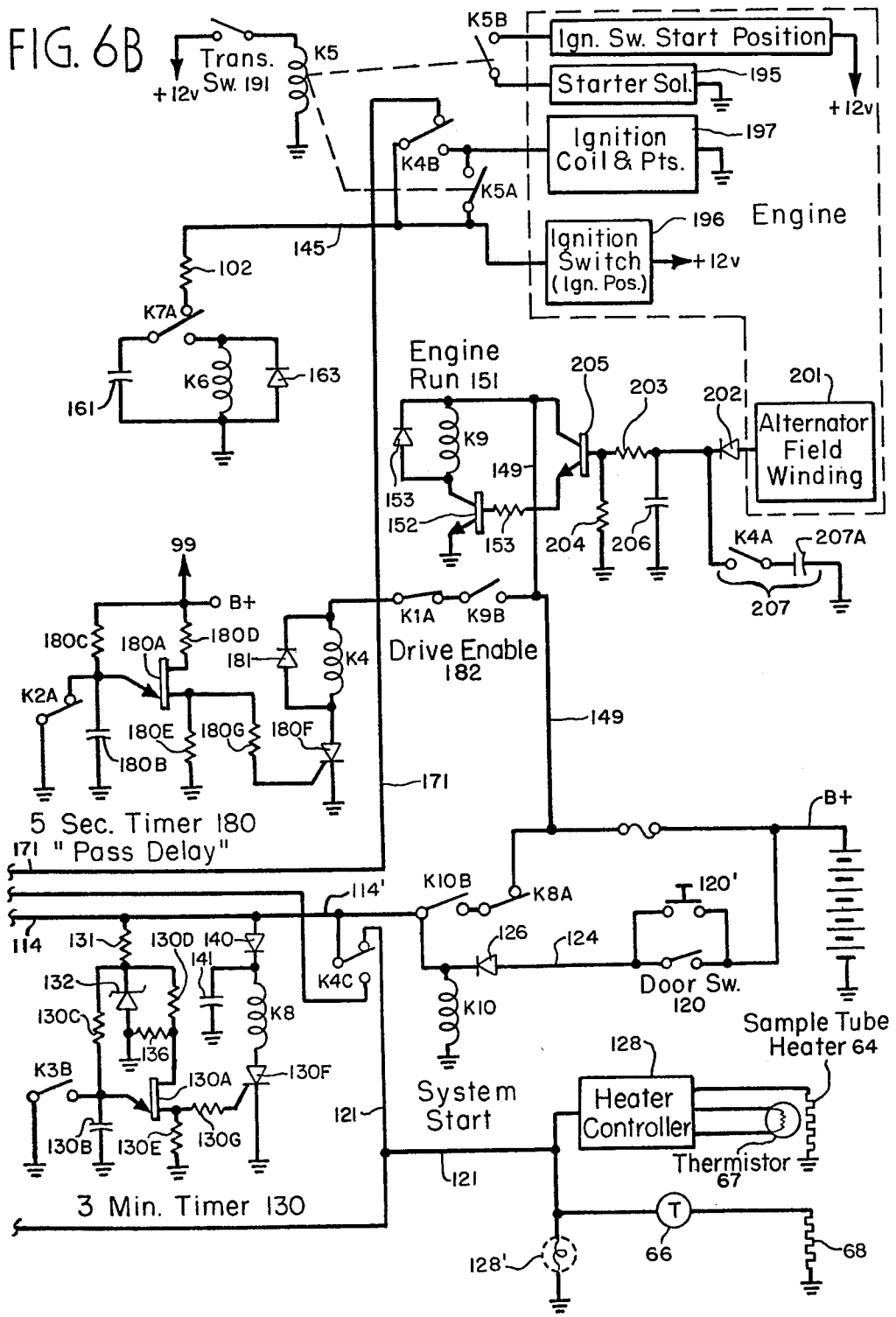

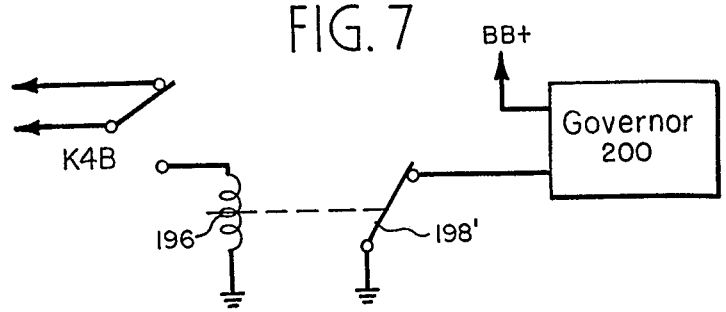
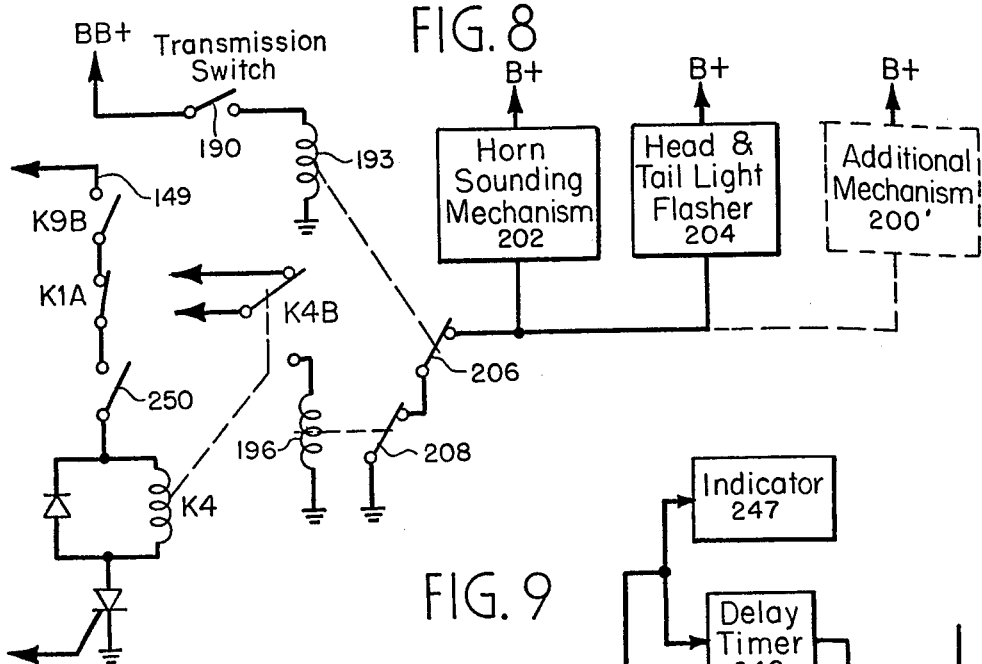
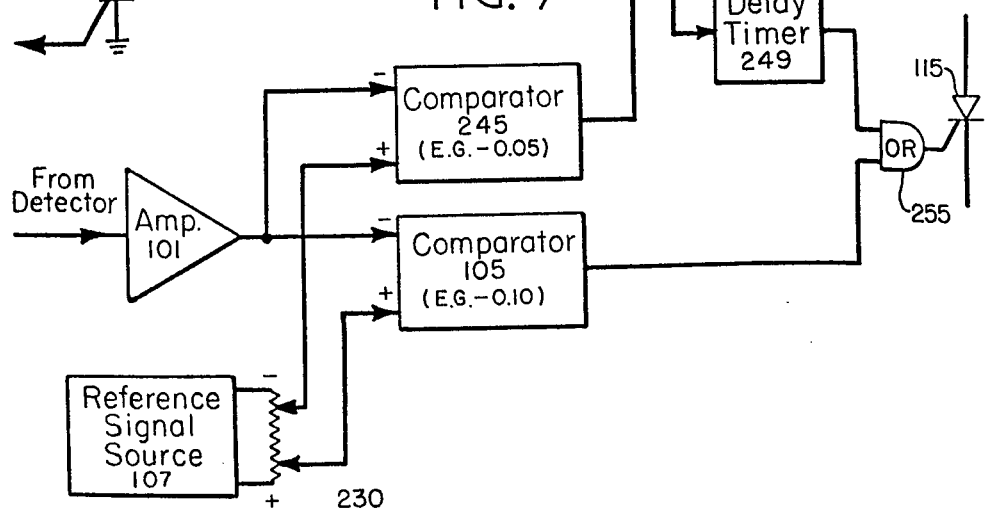

BREATH TESTING SYSTEM

CROSS-REFERENCE TO RELATED APPLICATIONS

The present application is related to copending U.S. Pat. application S.N. 136,778, which was filed on the same day as the present application in the names of the same inventors and the same assignee as the present application and S.N. 181,805 entitled "Breath Tester Null Memory System," filed Sept. 20, 1971 in the names of Joseph P. Hoppesch, Donald H. Ward and James R. Tomashek and having the same assignee as the present application.

FIELD OF THE INVENTION

The present invention is directed toward a new and improved breath testing system and inebriate driving inhibitor system.

BACKGROUND OF THE INVENTION

Alcoholic intoxication represents a major public health and safety problem in most countries in the world and especially in the United States of America. In America the motor vehicle is the principle means of transportation and millions of Americans drive their cars on the public highways each day. According to the American Medical Association's Committee on Medicolegal Problems publication, "Alcohol and the Impaired Driver," auto accident costs, in 1965 alone, exceeded eight billion dollars. In human terms, three and one-half million injuries were sustained in that year and 49,000 Americans were killed in auto accidents. Although the contribution of alcohol intoxication to this terrible toll cannot be precisely determined, there is general agreement that, despite stringent anti-drunk driving laws, alcohol intoxication is a factor in a major portion of these accidents.

As the population and number of automobiles increase, the problem of the drunk driver and the effect of his driving on innocent victims will intensify. By 1975 it is estimated that 225,000,000 Americans will ride in 113,642,000 motor vehicles with 80 percent of both of these in the crowded metropolitan areas. Controlling drunk driving will, at that time, be imperative.

While various proposals and devices have been made in the past to deal with detection and control of the inebriate, these have suffered from several drawbacks. Chemical testing devices tend to be inconvenient, difficult and sometimes dangerous for use by any but a well-trained technician. These devices also tend to be prohibitively expensive to be placed in the ordinary passenger automobile. Most of these devices allow for avoidance of an accurate test except in the case of direct and alert supervision. For example, breath tests to be accurate require a deep lung breath sample and can be evaded by inhaling and exhaling repetitively so as to test only oral or mixed breath. Other testers (such as that shown in U.S. Pat. No. 3,311,187), which involve agility, memory, eyesight and/or reaction-time testing do not test alcoholic intoxication as legally defined and allow for errors of inclusion and exclusion.

The term "gas," as used herein and in the appended claims, embraces both ordinary air in the atmosphere, and breath exhaled from the lungs of a human subject.

"Vehicle," as used herein and in the claims, means any human-guided self-propelled unit, such as an automobile, train, airplane, motorboat, on-and off-the road unit, such as a snowmobile or bulldozer, and the like.

SUMMARY OF THE INVENTION

To meet the growing problem of drunk driving, the present invention provides a relatively simply operated, accurate and economic breath tester that provides a direct measurement of deep lung breath alcohol level without the necessity of close supervision of the subject. An inebriate inhibitor system constructed according to the present invention includes a breath input unit, a controller, an alcohol level evaluator and an output unit intercoupled so as to test a breath sample from the input unit only after a continuous flow of breath into the input unit, (as, e.g., provided by a pressure switch or the like) for a predetermined period, such as 2–8 seconds, so that a sufficient breath sample is taken and fed to the detector of the evaluator. Interruption of the breath flow, as to attempt to inhale air, causes the controller to recycle and require another such period of continuous flow. The system preferably includes as part of the evaluator a comparator coupled to the detector and coupled to a reference signal source for producing an output signal indicative of "pass" or "fail" when the tested breath sample falls below or above a preselected alcohol level.

In accordance with one feature of the invention the system may include controls, as part of the output unit, that modify a vehicle's operation in the absence of a required pass output signal.

Thus, in the absence of a required pass signal from the comparator of the system, the vehicle may be prevented from starting, prevented from operating in any drive gear, governed to run only at low speeds or caused to emit a warning, such as flashing of its lights and/or signaling with an alarm. The invention, together with further advantages and features thereof, may best be understood by reference to the following description taken in connection with the accompanying drawings, in the several figures of which like reference numerals identify like elements.

BRIEF DESCRIPTION OF THE DRAWINGS

FIGS. 6A and 6B, taken together, disclose a circuit diagram of one embodiment for the system of FIGS. 1–5B;

FIG. 7 is a partly schematic and partly block diagram of a modification of the system of FIGS. 1–6B illustrating another embodiment of the invention;

FIG. 8 is partly schematic and partly block diagram of another modification of the system of FIGS. 1–6B illustrating another embodiment of the invention; and FIG. 9 is a partly schematic and partly block diagram of a further modification of the system of FIGS. 1–6B illustrating yet another embodiment of the invention.

DETAILED DESCRIPTION

Figure 1:
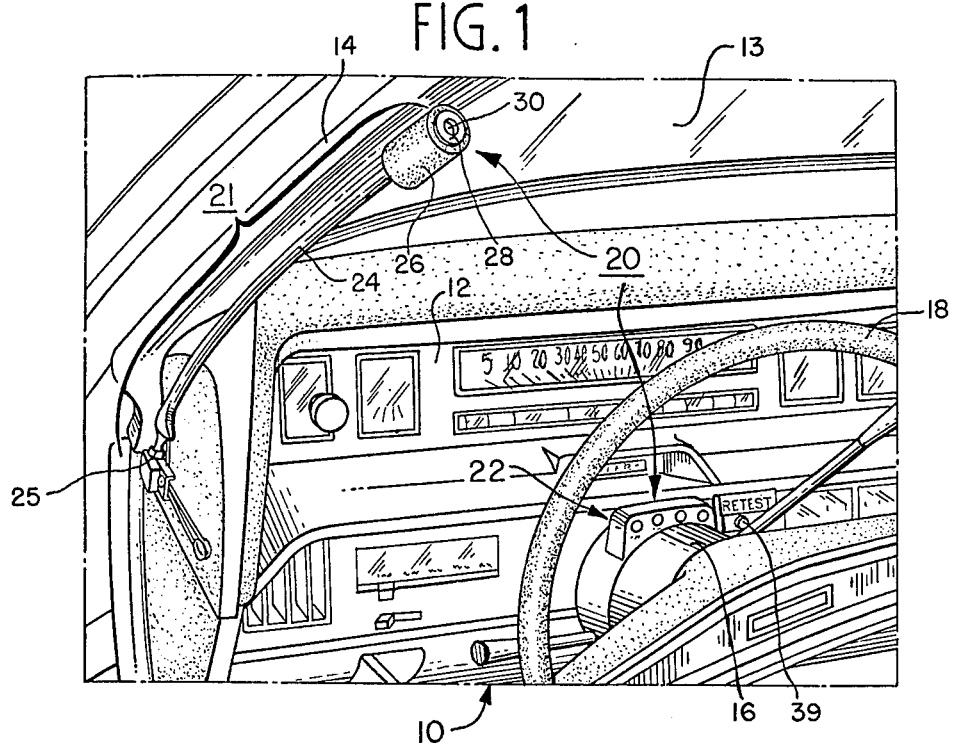
FIG. 1 is a perspective partial view of an automobile showing the dash section thereof, which automobile includes a breath testing system constructed in accordance with the present invention.

Referring to FIG. 1, there is depicted a vehicle generally designated by the number 10. The vehicle 10, as depicted, is a passenger automobile which includes a conventional dash 12, windshield 13, driver's side windshield post or A pillar 14, steering column 16 and steering wheel 18.

In accordance with the present invention, the vehicle 10 is equipped with a breath testing system which is generally designated by the numeral 20 and part of which is mounted within the dash 12. The portion of the system 20 depicted in FIG. 1, includes a breath input unit 21 and signal output unit 22. The input unit 21 preferably includes a tube structure 24 having one end 25 secured to dash 12. The other end of the tube 24 is unsecured and, has a cylindrical shaped end piece or handle 26.

At the extreme end of the handle 26 is a disc shaped cap 28 in which a breath input opening 30 is formed. As will be explained in more detail in conjunction with the description of FIG. 4, the opening 30 is in communication with the portion of the system 20 within the dash via a passageway through the handle 26, tube 24 and its end segment 25.

Figure 1A:
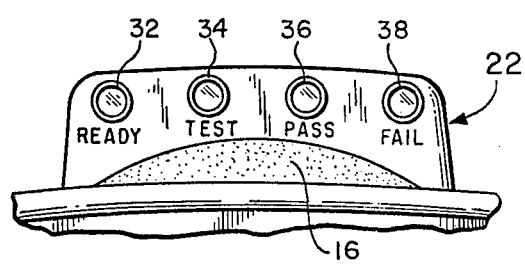
FIG. 1A is an enlarged elevational view of one portion of the system shown in FIG. 1.

The signal output unit 22 as best shown in FIG. 1A includes a set of indicating lights: a "Ready" light 32, a "Test" light 34, a "Pass" light 36 and a "Fail" light 38. The output unit 22 is shown mounted on the steering column 16; however, it may be mounted in any convenient position where it is visible to the driver of the automobile 10. The lights 32, 34, 36 and 38 may be of different colors and are preferably respectively, amber for test, green for pass, red for fail and white for ready.

A "Retest" pushbutton switch 39 may also be provided as part of the system, preferably mounted so as to be easily accessible to the driver, such as shown in FIG. 1, mounted on the dash 12.

Figure 2:
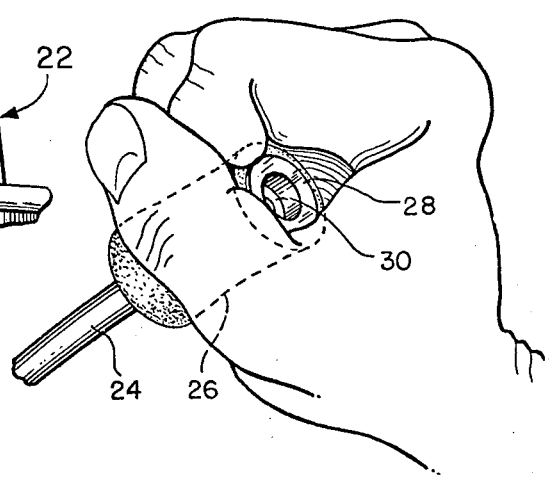
FIG. 2 is a perspective view of a portion of the input unit of that breath testing system of FIG. 1 being gripped by a hand and illustrating the manner in which the device may be used in a sanitary manner.

As best shown in FIG. 2, the cylinder shaped handle 26 of the input unit 21 is adapted so as to be grasped in one hand of the user with the thumb and curving index finger projecting above the opening 30 to form a ring for guarding the lips of the user from direct contact with the handle 26. The body of the handle 26 is preferably formed of resilient compressible material such as foam or sponge rubber and is relatively impervious to breath flow. By closing the fist about the handle and compressing the material, a good seal is formed between the hand and the handle. When used in this manner, as shown better in FIG. 3, the driver or user may blow air into his cupped hand and into the input unit 21 in a sanitary manner without having his lips touching the input unit 22.

Figure 3:
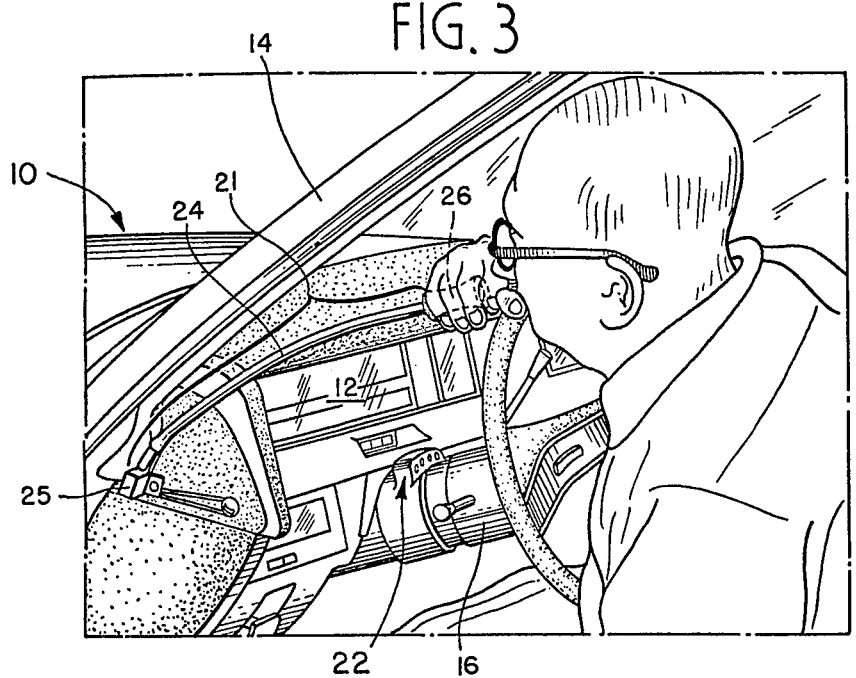
FIG. 3 is a perspective view, similar to that of FIG. 1, showing a subject using the input unit of the system.

The tube 21 is preferably made to be resiliently bendable from its normal rest or storage position along and adjacent to the A post 14 (as shown in FIG. 1) to a bowed position over the steering wheel for use (as shown in FIG. 3) by the driver whose breath is to be tested.

Figure 4:
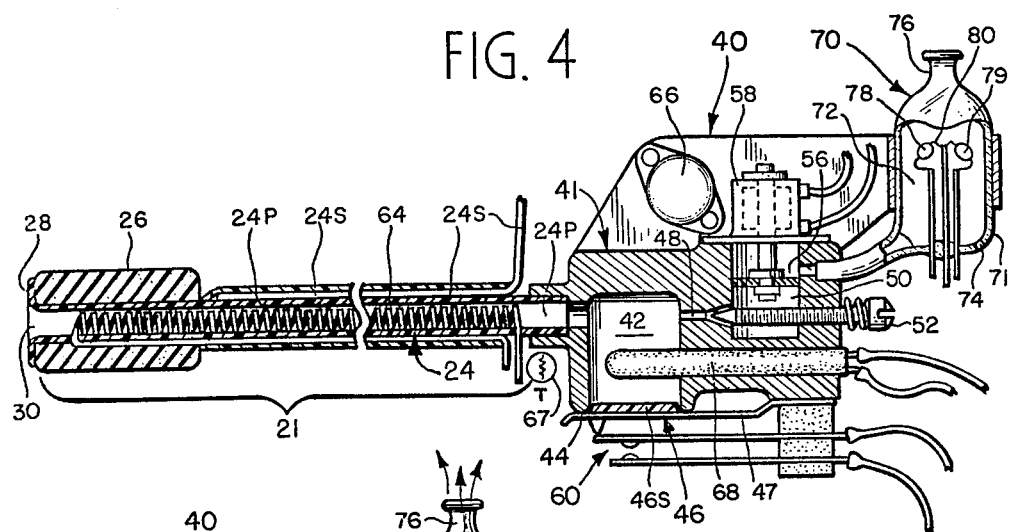
FIG. 4 is a partially sectional view with parts broken away of a portion of the system of FIGS. 1–3, including a controller portion that is hidden from view in those figures.

The required resiliency can be provided by choosing a resilient material such as plastic or rubber for the tube 24. The tube 24 may be reinforced by means of a spring metal wire or hairpin spring 24S affixed along the tube 24, as shown in FIG. 4, or by other means. It should be noted that this storage position for the input tube makes it readily available for use but does not interfere with the driver's vision or operation of the vehicle. The input unit 22 is claimed in application S.N. 197,408, filed Nov. 10, 1971, entitled "Breath Input Hand Unit for Breath Tester," of common assignee.

Figure 5:
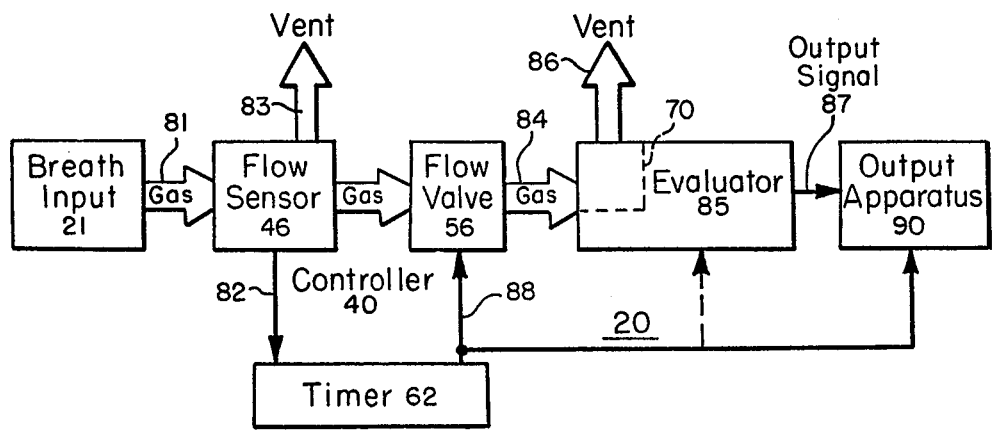
FIG. 5A is a block diagram illustrating the system of FIGS. 1–4.
FIG. 5B is a partial block diagram similar to FIG. 5A, but illustrating one particular output apparatus, a meter.

Referring now to FIG. 4 there is depicted the input unit 21 and additional components of the system 20: a controller 40 and a detector 70, both of which are housed within the dash 12 of the automobile. As will be explained below in conjunction with the discussion of FIG. 5A, the detector 70 forms part of a breath evaluator 85 that evaluates the alcohol content of the breath.

As is best shown in FIG. 4, the tube structure 24 of the breath input unit 21 extends through the center of the handle 26. While the tube structure is preferably made of a flexible material so as to bend down, as shown in FIG. 3, the tube is sufficiently rigid to prevent it from being closed off by a hand gripping the handle portion 26.

Breath exhaled or blown into the input unit 21 is directed from the opening 30 through the tube structure 24 into the controller 40 via a passageway, designated 24P.

The controller 40 is a major feature of the present invention and includes the main body 41 which defines the chamber 42 into which the tube 24 channels the exhaled breath or gas flow. The chamber 42 has a first exit port 44 which may be closed by a flapper valve 46. The valve 46 comprises a leaf spring 47 attached to the body 41 on one end and having a valve portion 46S on the other end. The leaf spring 47 urges the valve portion 46S to close the port 44 under normal conditions. The vent 44 is open to the atmosphere when the valve portion 46S is unseated and serves to dump or vent gases from the chamber 42. The chamber 42 and the exit port 44 also serve to effectively remove and drain gas-flow-carried water and saliva from the subject's breath and prevent that moisture from interferring with the detector 70.

A second exit from the chamber 42 is provided by the orifice 48 which opens into a second chamber 50. A screw adjustable valve 52 is provided for adjusting the flow through the orifice 48. The chamber 50 is otherwise closed except for a port 54 which is opened and closed by means of a valve 56 actuated by a solenoid 58.

The flapper valve 46 functions to spill or vent at least the majority of the air or breath entering into the chamber 42. In so doing the breath pressure maintains the valve 46 open and closes a pair of electrical switch contacts 60. The flapper valve 46 thus serves as means for while maintaining the pressure within the chamber at a level above the atmospheric pressure, and also serves as means for indicating and signaling gas flow and pressure above a threshold level. In one working prototype this threshold level was set at a pressure of 3 inches of water with good results. Should the breath flow be interrupted, the pressure in chamber 42 falls below this threshold level causing the spring 47 to at least partially close the valve 46 and break the contacts 60.

Figure 4A:
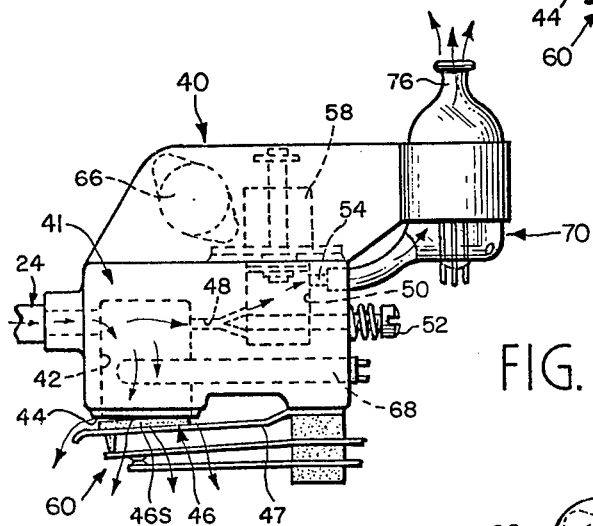
FIGS. 4A and 4B are elevational and diagramatic views with interior parts shown in phantom lines of the controller and detector portions of the device depicted in FIG. 4 illustrating breath flow paths and moved position of parts for different stages in the operation of the controller.
Figure 4B:
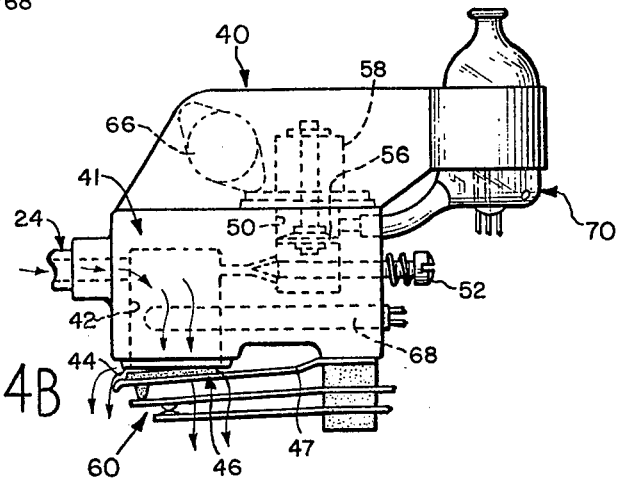

The operation and interrelation of the various parts of the controller 40 may be better understood by reference to the views of the controller 40 shown in FIGS. 4A and 4B. As shown in FIG. 4A, the controller 40 is shown in use, as at the start of the testing of a subject, with a gas flow and pressure communicated from the tube 24 which pressure is above the threshold level of the flapper valve 46. This pressure moves the valve portion 46S of the valve 46 opening the port 44 and closing the contacts 60. The closure of the contacts 60 energizes the solenoid 58 as will be explained in detail hereinafter which raises the valve 56. When this occurs gas also flows from the chamber 42 through the orifice 48 and chamber 50 to the port 54.

The closing of the contacts 60 is also signaled to a timer 62. If this signal is uninterrupted for a predetermined period, the timer de-energizes the solenoid 58 and lowers the plunger valve 56, as shown in FIG. 4B. However, if the flow is interrupted sufficiently to allow the contacts 60 to open before the predetermined period is over, the timer is reset. If closed again, the contacts must remain closed for a new interval of time of that predetermined period. Unless this prerequisite is satisfied, a "pass" signal cannot be provided. The gas present in the detector 70 at the end of a predetermined period of, for example, 5 seconds of uninterrupted blowing is essentially deep lung breath from which an accurate reading of blood alcohol level may be, as is well known in the art, inferred. In one actual embodiment this period of five seconds was employed with good results, although for different embodiments with different resistances to breath flow, periods varying from two to eight seconds, may be advantageously employed.

Thus, the controller 40 defeats any attempt of an unsupervised or ineffectively supervised subject to prevent an accurate test of deep lung breath by expelling, for a short period, oral and bronchial breath, stopping and inhaling fresh air and then exhaling this fresh oral and bronchial breath into the input unit 21, and repeating the process over and over again. It should be noted that, unlike some prior art testers, such as the balloon and bag types, closing off the input 30 of the input unit 21 between short blowing periods will not defeat the controller 40.

The controller 40 and breath input unit 21 of FIG. 4 are provided with a series of heaters and temperature sensors. Thus, as shown in FIG. 4, a spiral heater coil 64 is wound about the inner surface and along the length of the passageway 24P of the input unit 21; a thermistor 67 is mounted adjacent to the tube 24 for sensing the temperature of the tube and controlling the operation of the heater coil 64. A thermostat or temperature sensitive switch 66 is positioned adjacent to the outer surface of the body 41 of the controller 40 for sensing the temperature of the controller's environment, and a cartridge heater 68 is positioned in the body 41 and extends into the chamber 42 of the controller 40. The thermistor 67 and thermostat 66 are both temperature sensors and respectively control the heaters 64 and 68 to provide heat in the input unit 21 and the controller 40 to prevent condensation in unit 21 and controller 40 and thus preserve the integrity of the sample that eventually enters the detector 70.

As also best shown in FIG. 4, the detector 70 includes a chamber 72 preferably formed by a glass envelope 71. The chamber 72 is in communication with the chamber 50 through a tube segment 73 that opens into the port 54. Envelope 71 defines a series of small openings 74 at the bottom of chamber 72. The chamber 72 is open to the atmosphere through a main exit orifice 76.

The detector 70, after use, vents samples of breath primarily through the upward facing opening 76 by convection with fresh air entering mainly through the small holes 74. The relative size of these openings 74 are such as to not interfere with the test, but to provide sufficient circulation to purge the chamber.

Within the detector chamber 72 are positioned a catalyst resistance element 78 and a non-catalytic but otherwise identical resistance element 79. Since these two elements are both exposed to the sample simultaneously, effects such as thermal conductivity, convection, etc., are balanced out. These elements 78, 79 are preferably, respectively a catalyst coated ceramic bead containing a resistance wire and a non-catalytic identical bead, which beads are connected at a junction 80 and form adjacent legs of a Wheatstone bridge.

The breath passes over the heated catalytic element where any alcohol present is oxidized. The heat of this oxidation reaction causes the temperature and thus the resistance of the element to change. When alcohol passes over the non-catalytic element, no oxidation occurs and its resistance remains unchanged. This unbalancing of the resistances results in a change in bridge output, which output constitutes an information signal, which signifies the alcohol concentration level in the sample of gas.

Although here described as a catalytic combustion detector, which has been found to be an advantageous detector and is the preferred detector to be used with the system 20, other types of detectors may be employed without departing from at least the broader aspects of the present invention.

Referring to FIG. 5A, the entire system 20 is there depicted. The input unit 21 and the controller 40 together comprise a breath receiving unit. The input unit 21 delivers gas, as indicated by the line 81, to the flow sensor 46 which signals that sufficient flow exists to a timer 62 as indicated by the line 82.

The gas from the input 21 is vented as indicated by the arrow 83 and is also delivered to flow valve 56. The valve 56 serves to pass the gas until a command or test taken signal, indicated by the line 88, is delivered from the timer 62. That gas is transferred, as indicated by the line 84 to the detector portion 70 of the breath evaluator 85.

The transferred gas flow is vented, as indicated by the arrow 86 from the evaluator 85. The evaluator 85 evaluates the alcohol level of the sample and produces an output signal 87 indicative of that level. This signal may be and preferably is a simple pass or fail output. This output is, as indicated by the line designated 87 in FIG. 5A, fed to the output apparatus 90 which in the described environment of use includes the vehicle operation governing mechanism and output display 22. The signal may also be a continuous signal and the output apparatus include a meter 90' (depicted in FIG. 5B) for indicating its amplitude. This could be done as shown in detail in the aforementioned copending Ser. No. 136,778 application or otherwise.

The command signal on line 88 also serves to affect the evaluator 85 or output apparatus 90 or both so as to allow a pass or fail to be indicated by those units.

Referring to FIGS. 6A and 6B one specific example of the system 20 is there depicted. One example for the evaluator 85 and for the output unit 90, which includes the light output 22, are there depicted in detail. All of the relay switches in FIGS. 6A and 6B are shown in their unenergized position. That is, if they are normally open or normally closed, they are depicted as open or closed. The Wheatstone bridge, in addition to the ceramic-coated resistances 78 and 79 includes three series connected resistors 91, 92 and 93 connected between lines 78' and 79' as well as a potentiometer 94 connected in parallel with the resistor 92.

The lines 78', 79' comprise the input to the bridge and are respectively connected through variable or trimming resistors 95 and 96 to, respectively, a plane of reference potential or ground and a line 99 which is connected to a regulated source 200 of positive d.c. voltage. The line 99 also serves to connect this potential to other components of the circuit notably timers 62, 180 and 150, and the amplifiers 101, 109 and comparator 105.

The output of the bridge is taken from the line 81' and the tap of the potentiometer 94 and this information signal is fed to an operational amplifier 101 whose output on line 103 is compared, in a comparator 105 with a reference signal on line 107' from a source 107, which includes an operational amplifier 109 whose negative primary input and primary output are connected together and to the comparator input and whose positive primary input is connected across a holding capacitor 111 to ground and also through a relay switch K6A to the output of the amplifier 101. The particular comparator 105 functions to produce an output signal when the input lead 103 is positive by a predetermined amount (e.g. 0.5v.) with respect to the voltage on the lead 107'.

The components 101, 109 and 105 as well as their interconnects are simplified in FIG. 6A. As it is well within the ordinary skill in the art to connect the operational amplifiers and comparators to achieve the described operation, these details are not here set out for reasons of brevity.

In terms of the overall system the output signal may be regarded as the signal developed between the lines 103 and 107' or can be considered to be the signal on line 87. That is, the comparator 105 may be considered part of the output apparatus 90 or part of the evaluator 85.

The output of the comparator 105 is the fail indicating output signal 87. This signal is fed to the control electrode of a silicon controlled rectifier (SCR) 115 (part of the output apparatus 90) whose cathode is grounded and whose anode is connected to one end of a relay coil K1. The other end of the coil K1 is connected through a relay switch K2B to a line 117. The relay coil K1 closes a relay switch K1C which controls the fail light 38. That coil K1 also opens a relay switch K1A in a drive enable circuit 182 to prevent the moving of the vehicle after a fail signal.

To understand how this is achieved in these circumstances one should note that the particular automobile 10 of this specific example of one manner of practicing the invention, has an automatic transmission of the conventional type wherein the automobile's engine may be started only in "neutral" or "park." This neutral switch is represented in FIG. 6B by the switch 191 and is closed when the transmission is in neutral or park. When closed the switch 191 connects positive potential to one end of a relay coil K5 whose other end is grounded. Energizing of the coil K5 allows the engine's start solenoid 195 to be energized through a normally open relay switch K5B. The coil K5 also closes a switch K5A to connect positive voltage from the vehicle's conventional ignition switch's ignition position contacts, indicated by the unit 196 in FIGURE 6B, to the engine's conventional ignition coil and points 197, which allows the ignition coil of the engine to be energized and the engine started. The ignition coil and points 197 may also be connected through the relay switch K4B upon energization of a relay coil K4. The relay formed by the coil K4 and its switches, including the switch K4B, may be a latching relay to prevent the engine from dying in the event of a component failure in the breath test system 20.

Thus, the engine may be started conventionally, but should the transmission switch be opened by moving it to a drive position without the switch K4B being closed, current will be cut-off from the ignition coil unit 197 and the engine will die. The switch K4B cannot be closed to connect potential to the ignition unit 197 unless the coil K4 is energized. That coil K4, however, cannot be energized if the coil K1 is energized in response to a fail signal and thus prevents the vehicle from being driven after a fail signal.

Of course, for other vehicles not having a transmission switch, equivalent means can be provided to, e.g., prevent the ignition from being operated or the gas pedal from being depressed after starting without passing the test.

Prior to the taking of the test by the driver, certain components must be in operating condition, that is, be prepared for operation and, a reference signal must first be developed from an air sample and stored on capacitor 111 of source 107. To achieve these ends certain sensors, timers and heaters are employed and these are depicted in FIGS. 6A and 6B Thus, the conventional door switch 120, which actuates the conventional automobile's dome light, designated by the numeral 128', is advantageously employed to indicate the possibility of a test. This switch 120 is connected to a source of voltage B+ such as the conventional automobile 12 volt battery and is also connected over a line 124 through a current blocking diode 126 to a system start relay coil K10. This coil closes a latching switch K10B which prevents deenergizing of the coil K10 by the closing of the door and resulting opening of door switch 120. The switch K10B is connected to a properly fused source of potential B+, which preferably is the automobile battery, through a normally closed relay switch K8A. For convenience of the user of the automobile an additional warm-up switch 120' may be provided electrically in parallel, and mounted, e.g., on the dash 12.

Closing of the switch K10B supplies voltage over a line 114 to the power regulator 200 that supplies the regulated potential to the line 99 and various components. Closing of the switch K10B, besides latching on the coil K10, also supplies the voltage over a line 114' to one side of relay coils K7 and K8 and, through the normally closed terminal of a relay switch K4C, to a line 121 to a heater controller 128 which controls the activation of the heater 64 in response to temperature sensor 67. The heater 68 is controlled by the thermostat 66 from voltage also supplied over the line 121. The dome light 128' is energized by current from the line 121 to light up the car interior during the test period. This feature tends to discourage cheating on the part of driver as it would make them readily visible at night.

Closing of the switch K10B also starts the long period timer 130. The period timer 130 includes its own regulated voltage supply including a resistor 131 connected between line 114 and the cathode of a zener diode 132 whose anode is grounded. The timer 130, as the structurally similar timers 62, 150 and 180, includes a timing resistor 130C one end of which is connected to the regulated voltage of the junction between the zener diode 132 and resistor 131. The other end of resistor 130C is connected to a charging capacitor 130B whose other side is grounded. The values of the resistor 130C and the capacitor 130B are chosen so as to raise, in the selected long period, the voltage across the capacitor 130B up to the firing level of a unijunction transistor 130A. The transistor 130A has its emitter connected to the junction of resistor 130C and capacitor 130B. The other terminals of the transistor 130A are biased by means of a resistor 130D connected between its base 2 and the bias source of zener diode 132, and a second resistor 130E connected between its base 1 and ground. The firing of the unijunction transistor 130A serves to turn on SCR 130F (via a resistor 130G, connected between base 1 and the gate of the SCR) which, in turn, allows current to flow momentarily from line 114 through the anode-cathode circuit of a diode 140 to a relay coil K8. Current from the line 114 through the diode 140 has previously charged a capacitor 141 connected from the cathode of the diode 140 to ground. Therefore when the SCR 130F is turned "on" and connects the one end of the coil K8 to ground, current also flows from the capacitor 141 through the coil K8.

As mentioned above, the normally closed switch K8A connects the line 114 to the source B+. This switch is opened by the energizing of the coil K8 to remove that voltage from the lines 114, and 121. This also de-energizes coil K10 and the switch K10B and removes potential from the heaters 64, 68 and the power regulator 200 and its supplied components. This restores the system to its starting condition.

Thus, if nothing else happens in the meantime, the long period timer 130 functions to restore the system to its starting condition the selected period (e.g., 3 minutes) after the door switch 120 was closed.

Thus, the driver on entering the car starts the self-regulated heaters 64 and 68 of the controller 40 and supplies power to the detector 70 and other components so that they may be ready to function should he desire to drive the vehicle. Should this be the case, the driver starts the engine of the vehicle.

After the engine is running for a warm-up period the "ready" light 32 will light informing the driver that the system 20 is ready for a test. To sense that the engine is running, a potential may be taken, for example, from the alternator field winding 201, and is applied through a diode 202 and voltage divider to the base of a NPN transistor 205 which is connected as an emitter follower with its collector connected to a line 149 from the potential source B+. A filter capacitor 206 is connected from the cathode of diode 202 to ground. This divider is made up of series connected resistors 203 and 204 connected from the cathode of the diode 202 to ground.

The transistor 205 is part of an "engine run" circuit 151 which includes a second NPN transistor 152 whose emitter is grounded and whose base is connected through a resistor 153 to the emitter of the transistor 205. The collector of transistor 152 is connected to one side of a relay coil K9 whose other side is connected to the B+ potential line 149. A safety diode 153' across the coil K9 has its anode connected to the collector of the resistor 153 and its cathode connected to the line 149.

The transistor 152 functions as a switch to energize the relay coil K9 and open the contact of a switch K9A which is part of the warm-up timer 150 and which starts that timer.

The timer 150 turns on the ready light 32, after a delay of a preselected period sufficient to place the system 20 in readiness. the timer 150 is similar to that of the long period timer 130 except for the value of components that determined a shorter warm-up period (e.g., 9 seconds). Thus it includes a unijunction transistor 150A, fired from a capacitor 150B which is charged from the regulated voltage source 99 through a resistor 150C. The unijunction transistor 150A has its bias established by resistors 150D and 150E and when fired turns on an SCR 150F through a resistor 150G, all of which components are connected in an analogous manner to the timer 130.

The SCR 150F, when turned "on", grounds one side of a relay coil K7 whose other side is connected to the line 114 resulting in energization of the coil K7. Energization of the coil K7 moves a relay switch K7A from its normally closed position to its normally open position. In its normally closed position switch K7A keeps a capacitor 161 charged by current communicated through a resistor 102 from a line 145 which is connected through the ignition switch 196 to B+. When moved to its normally open position, switch K7A causes capacitor 161 to discharge through another relay coil K6 protected by a safety diode 163.

The discharge of the capacitor 161 through the coil K6 momentarily closes the switch K6A and stores a first signal from the amplifier 101 on the capacitor 111. As mentioned before, this is the amplified output of the Wheatstone bridge of the detector 70 resulting from the air present therein prior to the sampling of breath. The momentary energizing of the coil K7 also closes a switch K7B which couples voltage from the line 145 through a normally closed contact of the switch K4B, a line 171 and a line 172 through a normally closed switch K2C to one side of a coil K3. The coil K3, like most of the relay coils, has a safety diode 173 connected across it. This also connects voltage to the ready light 32 and lights it.

The other side of the coil K3 is connected to the pressure switch 60 of the controller 40. The voltage supplied by the closure of K7B "arms" the pressure switch and allows it, on closing, to energize the coil K3 and opens the switch K3A and closes the switch K3B. This first switch K3A starts the timer 62, lights the "test" light 34, and energizes the solenoid 58. The latter switch K3B deactivates the three minute timer 130 by discharging the capacitor 130B.

The timer 62 is preferably structurally the same as the other timers differing only by the value of the resistance and capacitance in its timing circuit. That is, the timer 62 includes a timing resister 62C which feed current from the voltage source line 99 to a charging capacitor 62B. The capacitor 62B is connected to the emitter of a unijunction transistor 62A which is operationally biased by resistors 62D and 62E respectively connected from base 2 to line 99 and from base 1 to ground. Gate 1 of the unijunction transistor 62A is also connected through a resistor 62G to control an SCR 62F which alternatively isolates or grounds one end of a relay coil K2 whose other end is connected to the line 117. The line 117 is at a positive potential by means of the current path through the normally closed retest switch 39 and the line 171.

Closure of the pressure switch 60, thus initiates the timer 62 by the removal of ground from the junction of the resistor 62C and capacitor 62B. It also, by connecting of ground potential to another line 176, lights the test lamp 34 and communicates electrical potential over the lines 177, 178 to the solenoid 58 of the controller 40. (The solenoid 58 also preferably has a safety diode 58' connected across it.)

It should be noted that the solenoid actuated valve 56 is closed during the warm-up period and remains closed until the breath pressure switch is closed. The system 20 is so designed as to insure that air is tested at the end of the warm-up period. Although it might at first appear that the subject, by blowing before the ready light is on, may cause an erroneous "reference" to be taken, as the coil K7 closes both the switchs K7A and K7B at the same time, the operating time of the relay K3 may be chosen to be slow compared to the operating and release time of coil K6 to prevent this. The solenoid 58 may also be made slow acting to overcome this problem.

At the end of a short time period (e.g. 5 seconds) of continuous flow of breath, the timer 62 energizes the coil K2 which closes the switch K2B and supplies voltage to one side of the coil K1. The coil K2 also opens the switch K2A, initiating a timer 180. And it also opens the switch K2C to de-energize coil K3 and the solenoid 58 — closing the valve 56 and turning off the test light 34. light 34.

The closure of the valve 56 stops the flow of breath through the detector 70 and allows any cooling effect of that flow to be removed from the sensing resistance elements 78, 79. If, at any time during the period determined by the timer 180 (e.g., 5 seconds), the output of the detector 70, amplified by the amplifier 101, reaches the preselected alcohol threshold level, the comparator 105 produces the output fail signal and the SCR 115 is turned on. This energizes the relay K1 and opens the switch K1A of drive enabling circuit 182 to prevent automobile driving.

The timer 180 is structurally similar to the other timers, such as the timer 130, and includes a unijunction transistor 180A whose base 2 is biased by a resistor 180D connected to line 99; whose base 1 is connected through a resistor 180E to ground; whose emitter is connected to the junction of a resistor 180C and capacitor 180B. The other end of resistor 180C and the other side of capacitor 180B are respectively connected to line 99 and ground. The transistor 180A serves to turn on an SCR 180F by means of a resistor 180G connected between base 1 and to the control electrode of the SCR. This SCR 180F in turn, grounds or does not ground a relay coil K4 (which has a safety diode 181 connected across it).

At the completion of the pass delay period, the timer 180 energizes the coil K4 if the circuit is completed through the contacts of switches K1A and K9B to the source of B+ on line 149. The energization of the coil K4 causes the switch K4C to de-energize the heaters 64 and 68 and to turn on the pass light 36.

Thus to energize the relay coil K4 (which controls the switch K4B and thus permits the vehicle to be driven), switch K9B must be closed and the switch K1A must also be closed. This means that coil K1 must not be energized and coil K9 must be energized. That is, the fail signal from the comparator 105 must not be present and the engine must be running.

To prevent the necessity of re-taking a breath test in case the engine is stalled after a successful test, e.g., in traffic, a time delay unit 207 including, in the circuit of FIG. 6B, a capacitor 207A, one side of which is grounded and the other side of which is connected to a normally open relay switch K4A controlled by the coil K4. The other side of the switch K4A is connected to the junction of the diode 202, capacitor 206 and resistor 203.

When the test has been successfully taken, coil K4 is energized closing the switch K4A to add the relatively large time delay capacitor 207A to that of the capacitor 206. This capacitor 207A is charged during a short period by current from the alternator field winding 201. If the engine should die, this charge on capacitor 207A will maintain the Engine Run circuit on and the coil K9 energized for a predetermined period (e.g. 45 seconds) long enough to allow restarting without a re-test.

The stopping of the engine for a period long enough to open K9B de-energizes coil K4 opening the switch K4B and requires a new test for re-starting of the engine.

The functioning of system 20 can be seen from the following sequence of operations:

1. Open car door (switch 120, or push pushbutton switch 120'). This energizes the system start relay coil K10. The switch K10B holds coil K10 energized. The heaters 64, 68 are energized through their controls. Power is supplied through switch K10B to the power regulator 200 and its subsequent loads (amplifiers 101, 109, comparator 105 and the timers 62, 150 and 180).

2. The driver starts the engine. When the alternator voltage builds up, coil K9 energizes, switch K9A opens, starting the warm-up timer 150. After the warm-up period, coil K7 energizes. The switch K7A discharges capacitor 161 into coil K6, momentarily closing switch K6A which allows the bridge amplifier output to be stored by the capacitor 111 of the holding amplifier 109. The switch K7B turns on the ready light and arms relay coil K3.

3. The driver blows into the sample tube. The pressure switch 60 closes, energizing coil K3. The switch K3A turns on test lamp 34, the solenoid 58, opening the valve 56 and starts the 5 second timer 62. After 5 seconds, the coil K2 is energized. Switch K2C shuts off ready light 32 and relay coil K3. Switch K3A turns off the test light and de-energizes solenoid 58 causing the valve 56 to close. Switch K2B completes circuit to coil K1. Switch K2A starts the 5 second timer 180.

4. If a fail signal results at the comparator 105 output, coil K1 is energized. Switch K1A opens the circuit to coil K4 so that coil K4 cannot energize. Switch K1C turns on red fail light 38. If transmission lever is taken out of park or neutral the transmission relay K5 drops out, shutting off the engine. If the transmission is placed in park again, the engine can be restarted.

5. If the driver wishes to take another test, he presses the "retest" button 39. This de-energizes coils K2 and K1. The ready light 32 again lights. The driver repeats the test sequence.

6. If there is not a fail signal at the comparator 105 output, the 5 second timer 180 energizes coil K4. Switch K4A connects the delay capacitor 207A to the engine run sensing circuit 151. Switch K4C turns off the heaters and lights the pass light 36. Switch K4B maintains the engine ignition circuit energized when transmission is taken out of park or neutral.

7. If engine is accidentally stalled, the engine run remains closed for 45 seconds. Coil K4 remains energized through the switch K9B. The engine can be restarted and the car can be driven since the coil K4 is energized.

8. After 3 minutes from the last breath sample is taken the coil K8 energizes. Switch K8A opens the circuit to the coil K10 causing it to drop out. Switch K10B turns off the 3 minute timer and disconnects power from the regulator 200.

9. To reinitiate the system, the door must again be opened or the switch 120' closed.

Referring to FIG. 7 there is depicted a modified embodiment of the system of FIGS. 1–6B wherein the relay switch K4B instead of preventing the vehicle 10 from being driven unless the test is passed, allows the vehicle to be driven at all times. However, the vehicle may be driven only at low speeds (e.g., less than 10 mph.) unless the test is passed. A governor 300 is provided for the vehicle which governor is effective unless the switch K4B has energized a relay coil 296 and opened a switch 198'. When this occurs the governor is de-activated and the vehicle can be driven in a normal manner.

In FIG. 8 a further alternative for the output apparatus 90 is depicted where that apparatus serves to issue a warning that the automobile is being driven by one who has not passed the test. In this case the warning device is a horn sounding mechanism 302 and a head and tail light flashing mechanism 304. The mechanism 302 preferably sounds the horn intermittently. The mechanisms 302 and 304 may effectively employ bi-metal switches as the intermittent switching device or any well known equivalent. A pair of relay switches 306 and 308 are connected in series with the mechanisms 302 and 304. The switches 306 and 308 are respectively controlled by relay coils 193 and 296. The coil 296 is energized as was the case in the above, FIG. 7, embodiment by the relay switch K4B. The coil 193 is energized by the transmission switch 191. That is, when the conventional automatic transmission is put into park or neutral with the ignition switch on, the switch 191 is closed and the coil 196 energized. Both of these mechanisms 302 and 304 are energized if normally closed switches 306 and 308 are closed with the engine running. This occurs if the vehicle's automatic transmission is shifted out of neutral or park without the switch K4B being closed by a successfully passed test. Of course, in the case of a standard transmission, a switch such as the switch 191, may be added or a similar mechanism used to obtain the same result.

An optional feature, that may be employed in the system 20 is a driver seat pressure switch 250, (which preferably has a small delay) shown connected in series with the coil K4 in FIG. 8, that would require a second test if a driver who has passed the test leaves the driver's seat. Thus in response to the removal of pressure from the pressure switch 250 for longer than a predetermined short delay period, a new pass signal is required. This would prevent or make difficult an intoxicated driver from replacing one who has passed the test of the system 20. This optional feature is preferably employed only with the output apparatus such as that of FIGS. 7 and 8 to prevent disabling the automobile while in motion or in traffic. Of course additional mechanisms such as the mechanism 300' which may be the governor 300' (FIG. 7) or any other desired additional output apparatus can be employed in addition to, or in place of the mechanism 302 and 304.

The governor 300 may be of the cruise type, such as described in U.S. Pat. No. 3,388,764, for a desired speed and adapted not to be overriden by the accelerator pedal, or it may be a solenoid switch operating a conventional engine governor. Another alternative is a solenoid operated vacuum bellows transducer overriding the throttle control. Those skilled in this art will be able to provide equivalent governors. A collection of governors are briefly described in the paper "Choosing a Speed Governor" by Beryl A. Boggs, printed in the Mar. 18, 1963 issue of "Product Engineering" magazine.

FIG. 9 illustrates a further embodiment of the invention wherein, if desired, a further test of a driver may be required after a long period (such as 30 minutes), if he has initially tested over a certain intermediate alcohol level. This level may be below that thought desirable for activating the apparatus 90, but above the no alcohol level. Thus, a subject who has recently taken in a large quantity of alcohol or who continues to drink while driving his vehicle may initially test lower than the triggering level of comparator 105, but may later test higher. To prevent such a driver from driving, the modification of FIG. 9 may be employed wherein a comparator 245 triggered by an intermediate level of, e.g., 0.05 percent alcohol blood level, may be employed to start a timer 249 which will, after an appropriate delay institute the output apparatus 90 unless the test is taken over and passed. An appropriate indicator 247 (such as an initial warning light telling the driver that a retest will be needed and a second light somewhat prior to the end of the timer 249 period) may also be employed driven by the output of the comparator 245. This embodiment is preferably used only with the output apparatus of FIGS. 7 and 8 to prevent the disabling of a car in traffic.

For purposes of illustration and not limitation, the following values for the components of the system 20 are hereafter set out. These components were used in a working breath testing system and provided satisfactory performance. However, those skilled in this art will recognize that many alternative components and circuits could be employed without departing from the principles and scope of the present invention. For example, some or all of the relays could be replaced by solid state devices and the circuitry combined into integrated solid state circuits.

| Component | Value |
|---|---|
| Elements 78 and 79 | Minidetector (General Monitors, Inc.) |
| All Unijunction Transistors | 2N2646 |
| All Transistors | 2N3417 |
| All SCR's | C103YY (GE) |
| All Diodes | 1N4001 |
| Relay K6 | W101MPC-2 (Magnecraft) (Reed Relay) |
| Remainder of Relays | Km Type (Potter & Brumfield) (KM 5-D, KM 11-D and KM 14-D) |
| Amplifier 101 | Operational Amplifier MC1533G |
| Amplifier 109 | Operational Amplifier 1006-Phil.-Nexus |
| Capacitor 111 | 1.0 mfd. |
| Capacitor 161 | 500 mfd. |
| Capacitor 206 | 0.1 mfd. |
| Capacitors 62B, 180B | 25 mfd. |
| Capacitor 150B | 50 mfd. |
| Capacitor 130B | 530 mfd. |
| Resistor 150C | 150K ohms |
| Resistor 130C | 680K ohms |
| Resistor 62C | 100K ohms |
| Resistor 180C | 100K ohms |
| Resistors 203, 204 | 100K ohms |
| Resistors 130D, 136 | 270 ohms |
| Resistors 62E, 130E, 180E, 150E | 47 ohms |
| Resistors 62G, 130G, 180G, 150G, 102 | 470 ohms |
| Resistors 150D, 180D, 62D | 390 ohms |
| Resistor 93, 91 | 25 ohms |
| Resistor 92 | 4.5 ohms |
| Potentiometer 94 | 20 ohms |
| Variable Resistors 95, 96 | 0–20 ohms |
| Regulated Supply 200 | 9 v. |

The comparator 105 was made up of 2N3417 and 2N3906 transistors, resistor circuits and a 10 mfd capacitor.

The body 41 was made of aluminum for high thermal conductivity. The basic tube of the unit 21 was constructed of three-eighths inch (I.D.) Teflon plastic tube two feet in length. The heater 64 was of Nichrome brand wire.

Although the system has been described as being incorporated within the dash of an automobile, where it may well be placed as original equipment, it may also be packaged for retrofit into vehicles in which it was not incorporated as original equipment.

Although one particular detector, a catalytic oxidation detector, has been described others of this type are possible. The particular one employed is one in which two identical elements, one catalytic active and one passive are employed. Both elements comprise a resistance wire coated with a carrier such as $Al_2O_3$ and then one of the two is coated with a catalyst such as palladium. This particular detector, which is operated at about 400°C, has given satisfactory results. Others, such as one where the wire is the catalyst such as a fine platinum wire (the other wire being identical but coated with a non-catalyst such as gold), may also be employed. The detector may also use two or four elements. Thus, it could have two active and two passive elements in the cell, each of which forms the leg of a Wheatstone bridge. Of course, other bridge circuits may also be employed.

Other types of detectors than the catalytic oxidation detector may be employed without departing from the general principles of the present invention. Examples of these are the ionization type, (e.g., using a platinum filament to generate ions and measuring the ion current with an electrometer); the infrared radiation type disclosed, for example in U.S. Pat. No. 3,562,524 to Moore, et al.; electrochemical detector; or a chemiluminescense type detector. Still other types of detectors may be of possible use.

While particular embodiments of the invention have been shown and described, it will be obvious to those skilled in the art that changes and modifications may be made without departing from the invention in its broader aspects and, therefore, the aim in the appended claims is to cover all such changes and modifications as fall within the true spirit and scope of the invention.

What is claimed is:

1. An inebriate operation inhibitor system adapted for use in a vehicle comprising:
   a breath receiving unit adapted to receive breath from the driver of the vehicle;
   means for sensing breath flow through said breath receiving unit including means operative only in response to a predetermined, essentially continuous and uninterrupted flow of breath therethrough to produce a test taken signal;
   an evaluator coupled to said breath receiving unit to receive said breath therefrom to detect the alcohol concentration level of said breath;
   means associated with said evaluator for producing a signal determined by the alcohol concentration of said breath, said means producing a "fail" signal in the event said alcohol concentration is above a desired level;
   output apparatus coupled to said evaluator and to said breath flow sensing means responsive to a fail signal from said evaluator or the absence of said test taken signal to modify the operation of the vehicle, wherein the vehicle includes a door switch, the inhibitor system has at least one heater, and the vehicle door switch is used to institute operation of said heater.

2. Breath testing apparatus comprising:
   means defining an input into which breath in the form of exhaled gas may be blown;
   means for sensing the flow of gas through said input;
   an evaluator connected to receive a sample of the gas flowing through said input, for evaluating the alcohol concentration in the received gas sample, and for producing an output signal in response to the detected alcohol concentration;
   an output apparatus connected to receive the output signal from said evaluator; and
   means, operative in response to said flow sensing means, for insuring that said output apparatus is activated in response to the output signal of said evaluator resulting from a predetermined essentially continuous and uninterrupted flow of breath over a threshold level, including a timer which after being started and if not reset produces a control signal after the predetermined period of time, which timer is started by said flow sensing means sensing a gas flow above said threshold level, and is reset if said flow sensing means senses a gas flow below a predetermined level, and means, operative in response to the absence of the timer control signal, to prevent the evaluator from producing said output signal when the timer is reset before the expiration of the predetermined period of time.

3. Breath testing apparatus comprising:

means defining an input into which breath in the form of exhaled gas may be blown;

means for sensing the flow of gas through said input;

an evaluator connected to receive a sample of the gas flowing through said input, for evaluating the alcohol concentration in the received gas sample, and for producing an output signal in response to the detected alcohol concentration;

an output apparatus, connected to receive the output signal from said evaluator; and means, operative in response to said flow sensing means, for insuring that said output apparatus is activated in response to the output signal of said evaluator resulting from a predetermined essentially continuous and uninterrupted flow of breath over a threshold level, including a timer which after being started and if not reset produces a control signal after the predetermined period of time, which timer is started by said flow sensing means sensing a gas flow above said threshold level and is reset if said flow sensing means senses a gas flow below a predetermined level, and means, including a valve operative in response to receipt of the timer control signal, to control the gas flow from the breath input to the evaluator.

4. In a vehicle, the combination comprising:

apparatus for indicating the deep lung breath alcohol concentration of a subject, comprising:

a breath input unit for receiving a gas sample, means for providing a flow-indicating signal so long as the gas flow through the breath input unit is above a threshold level, an alcohol detector, connected to evaluate the alcohol concentration in gas received from the breath input unit, and to produce an information signal in response to the detected alcohol concentration, means for directing gas from the breath input unit to the alcohol detector, timing means, operative in response to receipt of the flow-indicating signal, for providing a control signal after the flow-indicating signal has been continuously present for a predetermined time period, so that a subject blowing breath continuously over the threshold level for the predetermined time period will provide a deep lung breath sample for testing in the alcohol detector at the time the control signal is provided by the timing means; and output apparatus coupled to the vehicle connected for operation in response to the receipt of the detector information signal and said control signal to modify the operation of the vehicle.

5. The invention as defined in claim 4, in which said timing means is started when said flow-indicating signal is initially provided, and is reset if said flow-indicating signal is removed; and means, operative in response to the receipt of the control signal from the timing means for allowing the production of a pass-indicating output signal, and in the absence of receipt of the control signal, for preventing the production of a pass-indicating output signal.

6. The invention as defined in claim 4, in which said timing means is started when said flow-indicating signal is initially provided, and is reset if said flow-indicating signal is removed; and means, including a valve operative in response to receipt of the control signal from the timing means, to control the gas flow from the breath input unit to the detector.

7. The invention defined in claim 4, and further comprising:

means for providing a reference signal; and a comparator in said output apparatus, which comparator is coupled both to the means for providing a reference signal and to said detector, for comparing the information signal with the reference signal and for producing a fail output signal whenever the information signal from the detector reaches a predetermined relationship with respect to the reference signal.

8. The combination of claim 7, which further includes:

means associated with said output apparatus for preventing the vehicle from being operated with a fail signal from said evaluator.

9. The combination of claim 7, wherein:

means associated with said output apparatus to give a warning when the vehicle is driven when a fail signal has been produced from said evaluator.

10. The combination of claim 9, wherein the vehicle includes headlights and tail lights and means are provided for intermittently energizing said lights as said warning.

11. The invention of claim 10, wherein the vehicle includes a horn and means are provided for sounding said horn as said warning.

12. The invention of claim 7, wherein:

means are associated with said output apparatus which govern the speed of the vehicle to prevent it from exceeding a predetermined value whenever it is operated after a fail signal from said evaluator.

13. The invention of claim 7, wherein:

said vehicle includes a door switch;

said apparatus has at least one heater, and said door switch is used to institute operation of said heater.

14. The combination of claim 7, wherein:

said vehicle includes a light for illuminating the operator; and means are provided for energizing said light during the at least part of the predetermined time period.

15. The invention of claim 7, wherein:

said vehicle includes a driver's seat;

said apparatus includes means or producing a pass signal in response to said information signal and said control signal;

a seat pressure switch in the driver's seat; and means are provided for, after a pass signal has been obtained, requiring a new pass signal, in response to the removal of pressure from said pressure switch for longer than a predetermined short period.

16. The combination of claim 4, wherein said vehicle includes an engine, and
timing means are provided coupled to said engine and to said output means to allow the engine to be restarted and the vehicle driven in an unmodified manner within a predetermined period after shut down of the engine.

17. The invention as defined in claim 4, in which the output apparatus includes means for indicating when the information signal received from the detector exceeds a predetermined level.

18. The combination defined in claim 7, wherein:
said apparatus includes another comparator coupled to the reference signal and the detector output signal, which another comparator produces an output signal when the detector signal reaches a value indicative of some preselected intermediate alcohol level less than that for said other comparator; and
a timer activated by the output of said another comparator to produce an output signal after a predetermined time.

19. An inebriate operation inhibitor system adapted for use in a vehicle comprising:
a breath receiving unit adapted to receive breath from the driver of the vehicle;
means for sensing gas flow through said unit and producing a signal in response thereto;
an evaluator adapted to receive gas flow through said unit and to produce a signal responsive to the alcohol content of said gas; and
means for modifying the operation of the car unless a pass signal is supplied to said last mentioned means, consisting of a signal from the evaluator below a predetermined level of alcohol concentration while the flow indication signal is above a threshold value.

20. An inebriate operation inhibitor system adapted for use in a vehicle comprising:
a breath receiving unit adapted to receive breath from the driver of the vehicle;
means for sensing gas flow through said breath receiving unit including means to signal the presence of gas flow above a threshold value;
an evaluator coupled to said unit to receive said gas therefrom and to detect the alcohol concentration level of said gas;
means associated with said evaluator for producing a signal determined by the alcohol concentration of said gas, said means producing a fail signal in the event said alcohol concentration is above a desired level; and
output apparatus coupled to said evaluator and to said gas flow sensing means responsive to a fail signal from said evaluator or the absence of said gas flow signal to modify the operation of the vehicle.

21. A breath alcohol detection system for motor vehicles comprising:
a sensor responsive to exposure to alcoholic vapor in a breath sample for producing a first electrical signal;
input means for communicating breath samples to the sensor;
means responsive to the application of a sample to said input means, for producing a second electrical signal independent of the alcohol content of the sample; and
logic means connected to simultaneously receive the first and second signals for producing an output condition to enable normal engine operation only when the combination of the first and second signals indicates a breath sample having less than a predetermined alcoholic content.

22. A breath alcohol detection system as defined in claim 21, wherein said means responsive to the application of a sample comprises:
a pressure switch having normally open contacts, said contacts being closed by and during the application of said sample.

23. A breath alcohol detection system as defined in claim 21, wherein said sensor comprises:
a detector element having a resistance characteristic which changes on exposure to an alcoholic vapor.

24. A breath alcohol detection system as defined in claim 23, wherein said input means comprises:
a housing having an inlet, an outlet, and a sensor chamber between the inlet and outlet, said detector element being disposed in said chamber; and
a restricted passage coupled to said inlet and chamber for communicating a breath sample into the chamber.

25. A breath alcohol detection system as defined in claim 24, wherein:
said restricted passage and said element are relatively disposed so that the sample avoids direct impingement on said element.

26. A breath alcohol detection system as defined in claim 24, wherein said means responsive to the application of a sample includes:
a pressure responsive switch connected to the inlet of the housing and responsive to the pressure of a breath sample to complete an electrical circuit therethrough.

27. A breath alcohol detection system as defined in claim 26, wherein:
said housing includes a bypass path connected to the inlet to bleed off a portion of the breath sample.

28. A breath alcohol detection system as defined in claim 21, including:
timing means connected between said means responsive to the application of a sample and said logic means for delaying the transmission of said second electrical signal to said logic means until said second electrical signal persists for a predetermined time.

29. A breath alcohol detection system as defined in claim 21, wherein said means responsive to the application of a sample includes:
a pair of normally open contacts:
pressure sensitive means connected between the input means and the contacts for closing the contacts when a breath sample is present:

a transistor having input and output electrodes; and means including a capacitive charging circuit connected between the contacts and input electrode to control the conductivity of the transistor when the contacts are closed long enough to charge the capacitive circuit.

30. A breath alcohol detection system as defined in claim 29, including:

reset means for discharging the capacitive circuit when the contacts are opened.

31. An ignition interlock system for preventing the operation of a motor vehicle until an operator submits a breath sample having less than a predetermined alcohol content comprising:

input means for receiving a breath sample;

a sensor operatively connected to the input means for exposure to the breath sample and responsive to the alcohol content thereof to produce an electrical signal quantity related to said content; and circuit means connected to operate on said electrical signal quantity to disable a vehicle engine from operating until a breath sample having less than a predetermined alcohol content is submitted.

32. A breath alcohol detection system for inhibiting the operation of the engine of a motor vehicle until the operator has submitted a deep lung breath sample comprising in combination:

a sensor device having a varying resistance characteristic upon exposure to alcoholic vapor in a breath sample for producing a first electrical signal representing the alcoholic content of a breath sample;

input means for communicating breath samples to the sensor;

means operatively associated with the input means and responsive to the application of a sample to said input means for producing a second electrical signal independent of the alcohol content of the sample;

said last mentioned means including timing means for producing said second electrical signal only after a predetermined period of application, thereby to ensure that the sample is alveolar breath; and logic means connected to simultaneously receive both the first and second signals and to logically combine such signals for producing an output condition to enable operation of the engine only when the combination of the first and second signals indicates a breath sample of said predetermined duration and having less than a predetermined alcohol content.

33. A breath alcohol detection system as defined in claim 32, wherein:

the timing means comprises a capacitor:

means for charging the capacitor during submission of a breath sample:

means for producing the second electrical signal only after the capacitor reaches a predetermined charge; and means for discharging the capacitor after application of the sample.

34. A breath alcohol detection system for motor vehicles comprising:

a sensor responsive to exposure to alcoholic vapor in a breath sample for producing a first electrical signal;

input means for communicating breath samples to the sensor;

means responsive to the application of a sample to said input means, for producing a second electrical signal independent of the alcohol content of the sample; and logic means connected to simultaneously receive the first and second signals for producing an output condition to enable normal vehicle operation only when the combination of the first and second signals indicates a breath sample having less than a predetermined alcoholic content.

* * * * *